United States Patent [19]

O'Donnell et al.

[11] Patent Number: 5,227,378

[45] Date of Patent: Jul. 13, 1993

[54] COMBINATION OF PAF ANTAGONISTS AND LTD$_4$ ANTAGONISTS FOR THE TREATMENT OF ALLERGIC REACTIONS

[75] Inventors: Margaret O'Donnell, Clifton; Ann Welton, North Caldwell, both of N.J.

[73] Assignee: Hoffmann-La Roche Inc., Nutley, N.J.

[21] Appl. No.: 848,564

[22] Filed: Mar. 9, 1992

Related U.S. Application Data

[63] Continuation of Ser. No. 561,743, Aug. 2, 1990, abandoned.

[51] Int. Cl.$^5$ .............................................. A61K 31/55
[52] U.S. Cl. ...................................................... 514/219
[58] Field of Search ......................................... 514/219

[56] References Cited
FOREIGN PATENT DOCUMENTS 0345931 12/1989 European Pat. Off. .

OTHER PUBLICATIONS

O'Donnell et al., Proceedings of the Fourth International Conference of the Inflammation Research Association held Oct. 23–27, 1988; Elsevier (Publisher), New York, Published Aug. 22, 1989.
Patterson et al., Int. Arch. Allergy Appl. Immunol., 88: 462–470 (1989).

*Primary Examiner*—S. J. Friedman
*Attorney, Agent, or Firm*—George M. Gould; George W. Johnston; William Krovatin

[57] ABSTRACT

The invention relates to compositions comprising combinations of a PAF antagonist and a LTD$_4$ antagonist which combinations synergistically provide protection against allergic reactions such as antigen-induced death in mammals.

In another aspect, the invention relates to the use of the referred to combinations in the treatment of allergic reactions.

2 Claims, No Drawings

COMBINATION OF PAF ANTAGONISTS AND LTD$_4$ ANTAGONISTS FOR THE TREATMENT OF ALLERGIC REACTIONS

This is a continuation of application Ser. No. 07/561,743 filed Aug. 2, 1990, now abandoned.

SUMMARY OF THE INVENTION

The invention relates to compositions comprising combinations of a PAF antagonist and a LTD$_4$ antagonist which combinations synergistically provide protection against allergic reactions such as antigen-induced death in mammals.

In another aspect, the invention relates to the use of the referred to combinations in the treatment of allergic reactions.

BACKGROUND OF THE INVENTION

The invention relates compositions comprising the synergistic combination of platelet activating factor (PAF) antagonists with leukotriene D$_4$ (LTD$_4$) antagonists and the use thereof to treat allergic reactions.

The mechanism of pathogenesis associated with allergic reactions involves an antigen-induced release of a variety of allergic mediators from mast cells, basophils, and possibly macrophages. These mediators include histamine, leukotrienes and PAF all of which posses a broad spectrum of potent biological activities. [Schleimer, R. P., Am. Rev. Respir. Dis., 133, 614–617 (1986)]. [Barnes, P. J., J. Allergy Clin. Immunol., 81,152–160 (1988)]. Assessment of the precise contribution of each individual allergic mediator to the pathology of allergic reactions is unknown.

For example, allergic asthma involves the antigen-induced release of allergic mediators from mast cell which subsequently cause bronchoconstriction, mucus secretion, and changes in capillary permeability which, in combination with the production of chemotactic agents, leads to the influx into the lung of inflammatory cells. The mediators rapidly induce a narrowing and occluding of the bronchial lumen of the airways and, over time, the development of a chronic inflammatory condition in the lungs. Inflammation of the airways may be essential to the establishment of bronchial hyperresponsiveness which is the characteristic abnormality of asthma. [Chung, K. F., Thorax, 41, 657–662 (1986)]. It has been difficult to identify the predominant mediator(s) of allergic asthma, but in recent years a number of lines of evidence strengthen the concept that the bronchoactive peptidoleukotrienes (LTC$_4$, LTD$_4$, and LTE$_4$) and PAF may be important in this disease process. LTD$_4$ and PAF have been identified in body fluids during an episode of asthma. They are both potent mediators of inflammation, and can reproduce some of the pathophysiological features of the disease when administered to animals and man. [O'Donnell, M. in Therapeutic Approaches to Inflammatory Diseases, A. J. Lewis, N. S. Doherty and N. R. Ackerman, eds., Elsevier Science Publishing Co., New York, 169–193 (1989)].

Compounds which prevent the effects of the mediators are thus of interest in treating allergic reactions. However, since allergic reactions are complex processes that are probably not attributable to a single causative factor, a potent, specific, agent by itself may not be particularly effective in preventing allergic reactions.

DETAILED DESCRIPTION OF THE INVENTION

Surprisingly, it has now been found that protection against allergic reactions such as antigen-induced death in mammals can be achieved by administering to such mammals an effective amount of a composition comprising a synergistic combination of a PAF antagonist and a LTD$_4$ antagonist.

In accordance with the invention, there can be used as the PAF antagonist component of a composition of the invention a known compound selected from the group consisting of:

5-{3-[4-(2-chlorophenyl)-9-methyl-6H-thieno[3,2-f][1,2,4]triazolo[4,3-a] [1,4]diazepin-2-yl]-2-propynyl} phenanthridin-6(5H)-one;

(R)-(2E,4E)-5-(4-methoxyphenyl)-N-[1-methyl-4-(3-pyridinyl)butyl]-2,4-decadienamide;

3-[4-[(R)-2-[(methoxycarbonyl)oxy]-3-[(octadecylcarbamoyl)oxy]propoxy] butyl]thiazolium iodide;

rac-4-{[6-(2-chlorophenyl)-8,9-dihydro-1-methyl-4H,7H-cyclopenta [4,5]thieno 3,2-f][1,2,4]triazolo[4,3-a][1,4]diazepin-8-yl]carbonyl} morpholine;

rac-N,N-dipropyl-6-{[6-(2-chlorophenyl)-8,9-dihydro-1-methyl-4H,7H-cyclopenta[4,5]thieno[3,2-f][1,2,4]triazolo[4,3-a][1,4]diazepine-8-carboxamide;

rac-6-(2-chlorophenyl)-8,9-dihydro-1-methyl-8-(4-morpholinyl)methyl-4H,7H-cyclopenta [4,5]thieno[3,2-f][1,2,4]triazolo[4,3-a][1,4]diazepine;

4-(2-chlorophenyl)-9-methyl-2-{2-[4-(2-methylpropyl)-phenyl]ethyl}-6H-thieno[3,2-f] [1,2,4]triazolo[4,3-a][1,4]diazepine;

4-(2-chlorophenyl)-6,9-dimethyl-2-{2-[4-(2-methylpropyl)phenyl]ethyl}-6H-thieno[3,2-f] [1,2,4]triazolo[4,3-a][1,4]diazepine;

2,3-dihydro-5-{4-[2-(3,4,5-trimethoxyphenyl)ethyl]-phenyl}imidazo[2,1-a]isoquinoline;

(2S,5S)-2-[(3-methylsulfonyl-5-methoxy-4-propyloxy)-phenyl]-5-(3,4,5-trimethoxyphenyl)tetrahydrofuran;

(+)-2-(2-acetyl-6-methoxy-3,9-dioxo-4,8-dioxa-2,10-diazaoctacos-1-yl)-1-ethyl, pyridinium chloride;

(+)-N-(3-benzoylphenyl)-3-(3-pyridinyl)-1H,3H-pyrrolo[1,2-c]thiazole-7-carboxamide;

1-O-hexadecyl-2(R,S)-O-ethyl-3-O-[7-(thiazolio-heptyl)]glycerol mesylate; and 1-acetyl-4-(8-chloro-5,6-dihydro-11H-benzo[5,6]cyclohepta[1,2-b]-pyridin-11-ylidene)piperidine.

Preferred PAF antagonists comprise the following compounds:

5-{3-[4-(2-chlorophenyl)-9-methyl-6H-thieno[3,2-f][1,2,4]triazolo[4,3-a] [1,4]diazepin-2-yl]-2-propynyl} phenanthridin-6(5H)-one;

(R)-(2E,4E)-5-(4-methoxyphenyl)-N-[1-methyl-4-(3-pyridinyl)butyl]-2,4-decadienamide;

3-[4-[(R)-2-[(methoxycarbonyl)oxy]-3-[(octadecylcarbamoyl)oxy]propoxy]butyl] thiazolium iodide; and (2S,5S)-2-[(3-methylsulfonyl-5-methoxy-4-propyloxy)-phenyl]-5-(3,4,5-trimethoxyphenyl)tetrahydrofuran.

Most preferred PAF antagonists are:

5-{3-[4-(2-chlorophenyl)-9-methyl-6H-thieno[3,2-f][1,2,4]triazolo[4,3-a] [1,4]diazepin-2-yl]-2-propynyl} phenanthridin-6(5H)-one; and (R)-(2E,4E)-5-(4-methoxyphenyl)-N-[1-methyl-4-(3-pyridinyl)butyl]-2,4-decadienamide.

Also, in accordance with the invention, there can be used as the LTD$_4$ antagonist component of a composition a known compound selected from the group consisting of:

(E)-4-[3-[2-(4-cyclobutyl-2-thiazolyl)ethenyl]-phenylamino]-2,2-diethyl-4-oxobutanoic acid;

rac-6-acetyl-7-[[5-(4-acetyl-3-hydroxy-2-propylphenoxy)pentyl]oxy]-3,4-dihydro-2H-1-benzopyran-2-carboxylic acid;

5-(3-(2-(7-chloroquinolin-2-yl)ethenyl)phenyl)-4,6-dithianonanedicarboxylic acid, mono N,N-dimethylamide, sodium salt;

[3-[[2-methoxy-4-[[[(2-methylphenyl)sulfonyl]amino]carbonyl]phenyl]methyl]-1-methyl-1H-indol-5-yl]-carbamic acid, cyclopentyl ester;

(E)-4-[3-[2-(4-(1-methylethyl)-2-thiazoyl)ethenyl]-phenylamino]-2,2-diethyl-4-oxobutanoic acid;

5-[[2-[[4-(2-quinolinylmethoxy)phenoxy]methyl]-phenyl]methyl]-1H-tetrazole;

5-(7-(3-(quinolin-2-yl)methoxy)phenylmethoxy)-4-oxo-4H-1-benzopyran-2-yl)-1H-tetrazole;

3(S)-(2-(carboxethyl)thio-3-(2-(8-phenyloctyl)phenyl)-propanoic acid;

2(S)-hydroxy-3(R)-(2-(carboxethyl)thio)-3-(2-(8-phenyloctyl)phenyl)propanoic acid;

1-[2-hydroxy-3-propyl-4-[4-[2-[4-(1H-tetrazol-5-yl)butyl]-2H-tetrazol-5-yl] butoxy]phenyl]ethanone;

5-{3-[2(R)-(carboxyethylthio)-1(S)-hydroxypentadeca-3(E), 5(Z)-dienyl] phenyl}-1H-tetrazole 2-(3-(2-quinolylmethoxy)phenylamino)benzoic acid;

1,1,1-trifluoro-N-[3-(2-quinolinylmethoxy)phenyl]methanesulfonamide;

N-[3-[3-(4-acetyl-3-hydroxy-2-propylphenoxy)-propoxy]-4-chloro-6-methylphenyl]-1H-tetrazole-5-carboxamide, sodium salt;

8-[4-(4-phenylbutyloxy)benzoyl]amino-2-(tetrazol-5-yl)-4-oxo-4H-1-benzopyran;

N-[2,3-dihydro-3-(1H-tetrazol-5-yl)-1,4-benzodioxin-5-yl]-4-(4-phenyl butoxy)benzamide;

rac-7-[3-(4-acetyl-3-hydroxy-2-propylphenoxy)propoxy]-3,4-dihydro-2-methyl-4-oxo-8-propyl-2H-1-benzopyran-2-propanoic acid;

[[5-[[3-(4-acetyl-3-hydroxy-2-propylphenoxy)-propyl]thio]-1,3,4-thiadiazol-2-yl]thio] acetic acid;

9-(4-acetyl-3-hydroxy-2-propylphenoxymethyl)-3-((1H)-tetrazol-5-yl)-4H-pyrido[1,2-a]pyrimidin-4-one;

6-(2-cyclohexylethyl)-[1,3,4]-thiadiazolo[3,2-a]-1,2,3-triazolo[4,5-d]pyrimidin-9(1H)-one; and 1-[[2-(1-methylethyl)pyrazolo][1,5-a]pyridin-3-yl]-2-methyl-1-propanone.

Preferred LTD$_4$ antagonists comprise the following compounds:

(E)-4-[3-[2-(4-cyclobutyl-2-thiazolyl)ethenyl]-phenylamino]-2,2-diethyl-4-oxobutanoic acid;

rac-6-acetyl-7-[[5-(4-acetyl-3-hydroxy-2-propylphenoxy)pentyl]oxy]-3,4-dihydro-2H-1-benzopyran-2-carboxylic acid; and 5-(3-(2-(7-chloroquinolin-2-yl)ethenyl)phenyl)-4,6-dithianonanedicarboxylic acid, mono N,N-dimethylamide, sodium salt.

A most preferred LTD$_4$ antagonist is:

(E)-4-[3-[2-(4-cyclobutyl-2-thiazolyl)ethenyl]-phenylamino]-2,2-diethyl-4-oxobutanoic acid.

The synergistic compositions and methods of the invention due to their antiallergic activity, can be utilized for the treatment of allergic disorders such as seasonal rhinitis, perennial vasomotor rhinitis, acute urticaria, chronic urticaria, atopic dermatitis, contact dermatitis, pruritis, angioedema, conjunctivitis, chronic bronchitis, systemic anaphylaxis, serum sickness, bronchial asthma, food allergies, and related inflammatory diseases including inflammatory bowel disease, and psoriasis.

The anti-allergic effect of the compositions of the invention comprising combinations of PAF antagonists and LTD$_4$ antagonists may be demonstrated utilizing procedures described hereinafter.

METHOD

A. Active Sensitization

Male (Hartley) guinea pigs (200–300 g) are sensitized with an intraperitoneal injection of ovalbumin (10 mg) in 1 ml of 0.9% w/v NaCl solution (saline) on days 1 and 3. The animals are used for the test on days 20–30 following the ovalbumin injections.

B. Pulmonary and Cardiovascular Mechanics

The sensitized guinea pigs are anesthetized with an intraperitoneal injection of urethane (2 g/kg), and polyethylene cannulae are introduced into both jugular veins and the right carotid artery. The arterial catheter is connected to a pressure transducer (Model 50, Statham Instruments, Inc., CA) for measurement to systemic blood pressure. The venous catheters are used for injection and infusion of the test composition.

The trachea is cannulated through an anterior cervical incision and positive pressure ventilation is applied with a Harvard pump set at a stroke volume of 4.5 ml and a rate of 40 breaths per minute. The respiratory muscles are paralyzed by periodic injections of succinylcholine chloride (1.2 mg/kg) given intravenously.

To measure transpulmonary pressure, a 12-gauge hypodermic needle attached via a short length of Tygon tubing to one side of a Statham differential pressure transducer (Model P131TC) is introduced through the fifth or sixth intercostal space into the intrapleural space near the sternum, leaving a pneumothorax. The other side of this transducer is connected to the sidearm of the tracheal cannula by a second Tygon tube of identical length and bore as the first. Airflow is measured with a Fleisch pneumotachograph head (type #0000, Instrumentation Associated, Inc., New York, NY) connected to a tracheal cannula and a second Statham differential pressure transducer (Model PM15). Electrical integration of the flow signal provides a recording of tidal volume.

Pulmonary resistance and dynamic lung compliance are calculated manually from the transpulmonary pressure, airflow, and volume signals as described by Amdur and Mead and the results are used to calibrate an on-line analog pulmonary computer (Buxco Electronics, Inc., Sharon, CO). [Am. J. Physiol., 192,364–368 (1958)]. Blood pressure is recorded with a cannula inserted into the carotid artery. Heart rate is calculated by an on-line analog cardiovascular computer (Buxco Electronics, Inc., Sharon, CO). All six parameters (airflow, transpulmonary pressure, tidal volume, resistance, compliance and blood pressure) are recorded simultaneously on a polygraph recorder (Model 7758A, Hewlett Packard, Paramus, NJ), and these parameters, plus heart rate and respiratory rate, are printed out on an electronic data terminal (Texas Instruments, Houston, TX). After completion of surgery, a period of no less than 5 minutes is allowed for cardiopulmonary functions to stabilize. During this period, control values are recorded continuously.

C. Challenge

Following surgical preparation, the animals are pretreated with intravenous indomethacin (10 mg/kg) 22 minutes before ovalbumin challenge presumably to shunt arachidonic acid from the cyclooxygenase pathway into the lipoxygenase pathway for the formation of leukotrienes, and to eliminate the modulating effects of prostaglandins. Spontaneous breathing is arrested with succinylcholine (1.2 mg/kg, i.v.) 7 minutes before antigen challenge. Treatment with succinylcholine results in a constant baseline ventilatory pressure of 6–8 cm $H_2O$. The bronchoconstrictor effects of histamine are abolished with pyrilamine (2.0 mg/kg, i.v.), administered 6 minutes before antigen challenge. To potentiate the bronchoconstrictor effect of antigen, propranolol (0.1 mg/kg, i.v.) is administered before antigen challenge. [Anderson, W. H., et al., Br. J. Pharmacol., 78,67–74 (1983)].

Various antagonists or control vehicle are administered intravenously through a cannula in the jugular vein 5 minutes before the animals are challenged with a maximum constrictory dose of ovalbumin (1 mg/kg) given intravenously.

The percent change in pulmonary resistance, dynamic lung compliance, and the systemic blood pressure and survival time are monitored for 120 minutes.

RESULTS

When the aforementioned model of anaphylaxis procedure was utilized to test various combinations of the invention, animals administered vehicle alone and challenged with antigen exhibited bronchoconstriction (approximately 550% increase in pulmonary resistance and 80% decrease in dynamic lung compliance), hypotension (55 mmHg decrease), and 83% mortality within 120 minutes. Table I contains the results obtained in this model with various combinations of the invention.

TABLE I

PROTECTION OF ANAPHYLACTIC DEATH IN SENSITIZED GUINEA PIG BY THE SYNERGISTIC COMPOSITIONS OF THE INVENTION

| COMPOUNDS | DOSE mg/kg. i.v. | COMPOUND | % SURVIVAL at 120 min. |
|---|---|---|---|
| ALONE* | | | |
| Control Vehicle | | | 17 |
| A | (1 mg/kg) | PAF antagonist | 0 |
| B | (1 mg/kg) | LTD₄ antagonist | 0 |
| C | (1 mg/kg) | LTD₄ antagonist | 50 |
| D | (10 mg/kg) | LTD₄ antagonist | 0 |
| E | (1 mg/kg) | PAF antagonist | 33 |
| F | (1 mg/kg) | PAF antagonist | 0 |
| G | (1 mg/kg) | PAF antagonist | 50 |
| COMBINATIONS OF THE INVENTION* | | | |
| A + B | | | 100 |
| A + C | | | 100 |
| A + D | | | 100 |
| B + E | | | 100 |
| B + F | | | 100 |
| B + G | | | 100 |
| C + G | | | 100 |

*COMPOUNDS
A 5-{3-[4-(2-chlorophenyl)-9-methyl-6H-thieno[3,2-f]1,2,4]triazolo[4,3-a][1,4]diazepin-2-yl]-2-propynyl}phenanthridin-6(5H)-one.
B (E)-4-[3-[2-(4-cyclobutyl-2-thiazolyl)ethenyl]phenylamino]-2,2-diethyl-4-oxobutanoic acid.
C 5-(3-(2-(7-chloroquinolin-2-yl)ethenyl)phenyl)-4,6-dithianonane dicarboxylic acid, mono N,N-dimethylamide, sodium salt.
D rac-6-acetyl-7-[[5-(4-acetyl-3-hydroxy-2-propylphenoxy)pentyl]oxy]-3,4-dihydro-2H-1-benzopyran-2-carboxylic acid.
E (R)-(2E,4E)-5-(4-methoxyphenyl)-N-[1-methyl-4-(3-pyridinyl)butyl]-2,4-decadienamide.
F 3-[4-[(R)-2-[(methoxycarbonyl)oxy]-3-[(octadecylcarbamoyl)oxy]propoxy]butyl]-thiazolium iodide.
G (2S,5S)-2-[(3-methylsulfonyl-5-methoxy-4-propyloxy)phenyl]-5-(3,4,5-trimethoxyphenyl)tetrahydrofuran.

The ability of the LTD₄ antagonist, compound B- (E)-4-[3-[2-(4-cyclobutyl-2-thiazolyl)ethenyl]-phenylamino]-2,2-diethyl-4-oxobutanoic acid, and the PAF antagonist, compound A- 5-{3-[4-(2-chlorophenyl)-9-methyl-6H-thieno[3,2-f][1,2,4]triazolo[4,3-a][1,4]diazepin-2-yl]-2-propynyl}phenanthridin6(5H)-one, to block antigen-induced bronchospasm, hypotension and death was evaluated at doses (1.0 mg/kg, i.v., 5 minute pretreatment) previously shown to completely inhibit bronchoconstriction induced by exogenous LTD₄ or PAF, respectively. Animals treated with compound B- (E)-4-[3-[2-(4-cyclobutyl-2-thiazolyl)ethenyl]-phenylamino]-2,2-diethyl-4-oxobutanoic acid or compound A- 5-{3-[4-(2-chlorophenyl)-9-methyl-6H-thieno [3,2-f] [1,2,4] triazolo [4,3-a] [1,4] diazepin-2-yl]-2-propynyl}phenanthridin-6(5H)-one alone had a 0% survival rate at 120 minutes, whereas when the combination was given, there was 100% survival at 120 minutes.

The ability of the LTD₄ antagonist, compound C- 5-(3-(2-(7-chloroquinolin-2-yl)ethenyl)phenyl)-4,6-dithianonanedicarboxylic acid, mono N,N-dimethylamide, sodium salt, and the PAF antagonist, compound A- 5-{3-[4-(2-chlorophenyl)-9-methyl-6H-thieno [3,2-f] [1,2,4] triazolo [4,3-a] [1,4]diazepin-2-yl]-2-propynyl} phenanthridin-6(5H)-one, to block antigen-induced bronchospasm, hypotension and death was evaluated at doses (1.0 mg/kg, i.v., 5 minute pretreatment) previously shown to completely inhibit bronchoconstriction induced by exogenous LTD₄ or PAF, respectively. Animals treated with compound C- 5-(3-(2-(7-chloroquinolin-2-yl)ethenyl) phenyl)-4, 6-dithianonanedicarboxylic acid, mono N,N-dimethylamide, sodium salt alone had a 50% survival rate at 120 minutes and those treated with compound A- 5-{3-[4-(2-chlorophenyl)-9-methyl-6H-thieno [3,2-f] [1,2,4] triazolo [4,3-a] [1,4] diazepin-2-yl]-2-propynyl}phenanthridin-6(5H)-one alone had a 0% survival rate at 120 minutes. However, when the combination was given, there was 100% survival at 120 minutes.

The ability of the LTD₄ antagonist, compound D-rac-6-acetyl-7-[[5-(4-acetyl-3-hydroxy-2-propylphenoxy)pentyl]oxy]-3,4-dihydro-2H-1-benzopyran-2-carboxylic acid, and the PAF antagonist, compound A- 5-{3-[4-(2-chlorophenyl)-9-methyl-6H-thieno [3,2-f] [1,2,4] triazolo[4,3-a][1,4]diazepin-2-yl]-2-propynyl} phenanthridin-6(5H)-one, to block antigen-induced bronchospasm, hypotension and death was evaluated at doses (10 mg/kg and 1.0 mg/kg, i.v., 5 minute pretreatment, respectively) previously shown to completely inhibit bronchoconstriction induced by exogenous LTD$_4$ or PAF, respectively. Animals treated with compound D- rac-6-acetyl-7-[[5-(4-acetyl-3-hydroxy-2-propylphenoxy) pentyl[oxy]-3,4-dihydro-2H-1-benzopyran-2-carboxylic acid or compound A- 5-{3-[4-(2-chlorophenyl)-9-methyl-6H-thieno[3,2-f][1,2,4]triazolo[4,3-a][1,4]diazepin-2-yl]-2-propynyl}phenanthridin-6(5H)-one alone had a 0% survival rate at 120 minutes, whereas when the combination was given, there was 100% survival at 120 minutes.

The ability of the LTD$_4$ antagonist, compound B- (E)-4-[3-[2-(4-cyclobutyl-2-thiazolyl)ethenyl]-phenylamino]-2,2-diethyl-4-oxobutanoic acid, and the PAF antagonist, compound E- (R)-(2E,4E)-5-(4-methoxyphenyl)-N-[1-methyl-4-(3-pyridinyl)butyl]-2,4-decadienamide, to block antigen-induced bronchospasm, hypotension and death was evaluated at doses (1.0 mg/kg, i.v., 5 minute pretreatment) previously shown to completely inhibit bronchoconstriction induced by exogenous LTD$_4$ or PAF, respectively. Animals treated with compound B- (E)-4-[3-[2-(4-cyclobutyl-2-thiazolyl) ethenyl]phenylamino]-2,2-diethyl-4-oxobutanoic acid alone had a 0% survival rate at 120 minutes and those treated with compound E- (R)-(2E,4E)-5-(4-methoxyphenyl)-N-[1-methyl-4-(3pyridinyl)-butyl]-2,4-decadienamide alone had a 33% survival rate at 120 minutes. However, when the combination was given, there was 100% survival at 120 minutes.

The ability of the LTD$_4$ antagonist, compound B- (E)-4-[3-[2-(4-cyclobutyl-2-thiazolyl)ethenyl]-phenylamino]-2,2-diethyl-4-oxobutanoic acid, and the PAF antagonist, compund F- 3-[4-[(R)-2-[(methoxycarbonyl)oxy]-3-[(octadecylcarbamoyl) oxy] propoxy] butyl] thiazolium iodide, to block antigen-induced bronchospasm, hypotension and death was evaluated at doses (1.0 mg/kg, i.v., 5 minute pretreatment) previously shown to completely inhibit bronchoconstriction induced by exogenous LTD$_4$ or PAF, respectively. Animals treated with compound B- (E)-4-[3-[2-(4-cyclobutyl-2-thiazolyl)ethenyl] phenylamino]-2,2-diethyl-4-oxobutanoic acid alone had a 0% survival rate at 120 minutes and those treated with compound F- 3-[4-[(R)-2-[(methoxycarbonyl) oxy]-3-[(octadecylcarbamoyl)oxy]propoxy]butyl] thiazolium iodide alone had a 0% survival rate at 120 minutes. However, when the combination was given, there was 100% survival at 120 minutes.

The ability of the LTD$_4$ antagonist, compound B- (E)-4-[3-[2-(4-cyclobutyl-2-thiazolyl)ethenyl]-phenylamino]-2,2-diethyl-4-oxobutanoic acid, and the PAF antagonist, compound G- (2S,5S)-2-[(3-methylsulfonyl-5-methoxy-4-propyloxy)phenyl]-5-(3,4,5-trimethoxyphenyl)tetrahydrofuran to block antigen-induced bronchospasm, hypotension and death was evaluated at doses (1.0 mg/kg, i.v., 5 minute pretreatment) previously shown to completely inhibit bronchoconstriction induced by exogenous LTD$_4$ or PAF, respectively. Animals treated with compound B- (E)-4-[3-[2-(4-cyclobutyl-2-thiazolyl)ethenyl] phenylamino]-2,2-diethyl-4-oxobutanoic acid alone had a 0% survival rate at 120 minutes and those treated with compound G- (2S,5S)-2-[(3-methylsulfonyl-5-methoxy-4-propyloxy)-phenyl]-5-(3,4,5-trimethoxyphenyl)tetrahydrofuran alone had a 50% survival rate at 120 minutes. However, when the combination was given, there was 100% survival at 120 minutes.

The ability of the LTD$_4$ antagonist, compound C- 5-(3-(2-(7-chloroquinolin-2-yl)ethenyl)phenyl)-4,6-dithianonanedicarboxylic acid, mono N,N-dimethylamide, sodium salt, and the PAF antagonist, compound G-(2S,5S)-2-[(3-methylsulfonyl-5-methoxy-4-propyloxy) phenyl]-5-(3,4,5-trimethoxyphenyl)tetrahydrofuran, to block antigen-induced bronchospasm, hypotension and death was evaluated at doses (1.0 mg/kg, i.v., 5 minute pretreatment) previously shown to completely inhibit bronchoconstriction induced by exogenous LTD$_4$ or PAF, respectively. Animals treated with compound C-5-(3-(2-(7-chloroquinolin-2-yl)ethenyl)-phenyl)-4,6-dithianonanedicarboxylic acid mono N,N-dimethylamide, sodium salt alone had a 50% survival rate at 120 minutes and those treated with compound G- (2S,5S)-2-[(3-methylsulfonyl-5-methoxy-4-propyloxy)phenyl]-5-(3,4,5-trimethoxyphenyl)tetrahydrofuran alone had a 50% survival rate at 120 minutes. However, when the combination was given, there was 100% survival at 120 minutes.

The compositions of the invention may be administered by any of the modes by which the individual components may be administered, for example, orally, intravenously or the like. The dosage regiment may be regulated according to the potency of individual compounds employed, the mode of administration, and the needs of the host mammal depending on factors such as the degree and the severity of the disease state and age and general condition of the host mammal being treated.

The compositions of the invention can be administered in unit dosage forms such as tablets, capsules, pills, powders, granules, sterile parenteral solutions or suspensions, suppositories, transdermal compositions, aerosols and the like. Such dosage forms are prepared according to standard techniques in the art.

The dosages may be varied depending upon the requirements of the host, the severity of the condition being treated and the particular compound being employed in the composition. Determination of the proper dosage for a particular administration is within the skill of the art. Generally, treatment is initiated at lower dosages and increased as needed by small increments until the optimum effect is reached. Exemplary dosages are in the range of from 0.1 to 4.0 gm per day of a combination of the invention. Exemplary dosages of the PAF antagonist can be in the range of 0.01 to 2.0 gms per day. Exemplary dosages of the LTD$_4$ antagonist can be in the range of 0.1 to 2.0 gms per day. Generally, the PAF antagonist is present in a ratio of from about 0.01 to about 50 parts to one part of the LTD$_4$ antagonist, preferably in a ratio of from 0.1 to about 10 parts to one part of the LTD$_4$ antagonist. For convenience, the total daily dosage may be administered in divided doses.

EXAMPLARY FORMULATIONS COMPRISING THE INVENTION FOLLOW

Example 1

| TABLET FORMULATION | | | |
|---|---|---|---|
| Item | Ingredients | mg/Tablet | |
| 1 | Compound A[(1)] | 0.1 mg | 250 mg |
| 2 | Compound B[(1)] | 1.0 mg | 250 mg |
| 3 | Croscarmellose Sodium* | 6.4 mg | 30 mg |
| 4 | Lactose | 100 mg | 255 mg |
| 5 | Avicel PH 101 | 20 mg | 60 mg |
| 6 | Methocel E15** | 1.5 mg | 9 mg |
| 7 | Magnesium Stearate | 1.0 mg | 6 mg |

TABLET FORMULATION -continued

| Item | Ingredients | mg/Tablet | |
|---|---|---|---|
| | | 130 mg | 860 mg |

*Other disintegrants, such as starch derivatives, Cross-Povidone, Amberlite, or similar in action may be used alone or in combination to obtain desired disintegration characteristics.
**Binders, such as pregelatinized starch or polyvinyl-pyrrolidone, etc., may be used to obtain a desired binding. Wetting agents, such as Tweens, spans, or sodium lauryl sulfate may be added to obtain desired disintegration and dissolution characteristics.
(1)As used hereinafter-
Compound A is 5-{3-[4-(2-chlorophenyl)-9-methyl-6H-thieno[3,2-f][1,2,4]triazolo[4,3-a][1,4]diazepin-2-yl]-2-propynyl} phenanthridin-6(5H)-one, and Compound B is (E)-4-[3-[2-(4-cyclobutyl-2-thiazolyl)ethenyl]phenyl amino]-2,2-diethyl-4-oxobutanoic acid.

Method of Preparation

1. Mix Items 1, 2, 3, 4, and 5 in a suitable mixer.
2. Granulate it with aqueous solution of Methocel E15.
3. Dry granulation at 45°–50° C.
4. Pass the granulation through a suitable mill.
5. Add Item 7 and mix.
6. Compress the granulation on a suitable tablet press.

Example 2

CAPSULE FORMULATION

| Item | Ingredients | mg/Capsule | |
|---|---|---|---|
| 1 | Compound A | 0.1 mg | 250 mg |
| 2 | Compound B | 1.0 mg | 250 mg |
| 3 | Pregelatinized Starch | 5 mg | 20 mg |
| 4 | Modified Starch | 5 mg | 20 mg |
| 5 | Talc | 4.4 mg | 20 mg |
| 6 | Lactose | 84 mg | 88 mg |
| 7 | Magnesium Stearate | 0.5 mg | 2 mg |
| | | 100 mg | 650 mg |

Method of Preparation

1. Mix Items 1, 2, 3, 4, and 6 and wet granulate with water.
2. Dry granulation at 45°–50° C.
3. Mill through suitable screen using appropriate milling equipment.
4. Add Items 5 and 7 and mix for 5 minutes.
5. Fill into suitable capsules.

Example 3

SOFT GELATIN CAPSULE FORMULATION

| Item | Ingredients | mg/mL | |
|---|---|---|---|
| 1 | Compound A | 0.1 mg | 250 mg |
| 2 | Compound B | 1.0 mg | 250 mg |
| 3 | Ethoxylated Fatty Acids | 50 mg | 250 mg |
| 4 | PEG-400 | 100 mg | 100 mg |
| 5 | Vegetable Oils q.s. to | 1.0 mg | 1.0 mg |

Method of Preparation

1. Add and mix Items 1 and 2 with Items 3 and 5.
2. Add Item 4 to the material from Step 1 and mix.
3. Add vegetable oil to the required amount.
4. Fill into a suitable capsule.

Example 4

ORAL SOLUTION FORMULATION

| Item | Ingredients | mg/5 mL | |
|---|---|---|---|
| 1 | Compound A | 0.1 mg | 100 mg |

ORAL SOLUTION FORMULATION -continued

| Item | Ingredients | mg/5 mL | |
|---|---|---|---|
| 2 | Compound B | 1.0 mg | 100 mg |
| 3 | Alcohol, Anhydrous | 10 mg | 500 mg |
| 4 | PVP K-30 | 10 mg | 500 mg |
| 5 | Aq. Sod. Hydroxide Solution | 1.0 mg | 100 mg |
| 6 | Sucrose | q.s. | q.s. |
| 7 | Flavoring Agent | q.s. | q.s. |
| 8 | PEG-400 q.s. to | 5.0 mL | 5.0 mL |

Method of Preparation

1. Dissolve Items 4, 6, and 7 in alcohol and PEG-400.
2. Add Items 1 and 2 and mix thoroughly.
3. Add Item 5 to material from Step 2 and mix until Items 1 and 2 dissolve.
4. Add PEG-400 to the required volume.
5. Fill the solution into a suitable container.

Example 5

PARENTERAL FORMULATION
(for I.V. or IM use)

| Item | Ingredients | mg/mL | |
|---|---|---|---|
| 1 | Compound A | 0.1 mg | 10 mg |
| 2 | Compound B | 1.0 mg | 10 mg |
| 3 | Benzyl Alcohol | 10 mg | 20 mg |
| 4 | Propylene Glycol* | 0.4 mL | 0.5 mL |
| 5 | Emulphor EL620** | 10 mg | 50 mg |
| 6 | Lactic Acid | 0.01 mL | 0.05 mL |
| 7 | Sod. Hydroxide pH to | 6-7 | 6-7 |
| 8 | Water for Injection q.s. to | 1.0 mL | 1.0 mL |

*Solvents or solubilizers, such as polyethylene glycols, alcohol, glycerine, Povidone, lecithin, sorbitan monooleate, or trioleate. Polysorbate 80 or 20 may be used in combination or alone to achieve the adequate solubility and stabilization.
**Powder for reconstitution may be formulated for appropriate solubilization or stabilization.

Method for Preparation

1. Dissolve Items 3, 4, 5, and 6 in water for injection.
2. Add and dissolve Items 1 and 2 in the solution from Step 1.
3. Adjust pH if necessary.
4. Add water for injection to the required volume.

Example 6

INHALATION AEROSOL FORMULATION
(Suspension)

| Item | Ingredients | % w/w | |
|---|---|---|---|
| 1 | Compound A, Micronized | 0.01 mg | 0.5 |
| 2 | Compound B, Micronized | 0.1 mg | 0.5 |
| 3 | Sorbitan Trioleate | 0.5 mg | 0.5 |
| 4 | Freon 11 | 19.39 mL | 18.5 |
| 5 | Freon 12 | 80 mg | 80.0 |
| | TOTAL | | 100% |

Method of Preparation

1. Mix Items 1, 2, 3 and 4 and homogenize thoroughly.
2. Fill the concentrate suspensin from Step 1 into a suitable can, place in valve, and crimp to seal container.
3. Pressure fill Item 5 to containers from Step 2.

Example 7

| INHALATION AEROSOL FORMULATION (Solution) | | | |
|---|---|---|---|
| Item | Ingredients | % w/w | |
| 1 | Compound A | 0.01 | 0.5 |
| 2 | Compound B | 0.1 | 0.5 |
| 3 | Ethyl Alcohol | 10 | 30.0 |
| 4 | Ascorbic Acid | 0.5 | 0.5 |
| 5 | Freon 114 | 20.0 | — |
| 6 | Freon 12 | 68.5 | 68.5 |
| | | TOTAL | 100% |

Method of Preparation

1. Dissolve Items 1, 2, and 4 in Item 3.
2. Fill solution from Step 1 into a suitable glass bottle, place in valve, and crimp to seal container.
3. Pressure fill Items 5 and 6 into the container from Step 2.

We claim:

1. A pharmaceutical composition useful in the treatment of allergic disorders comprising an effective amount of a combination of a PAF antagonist and a LTD$_4$ antagonist, wherein the amount of the PAF antagonist is in the range of from 0.01 to about 50 parts, to one part LTD$_4$ antagonist and wherein the PAF antagonist is 5-{3-[4-(2-chlorophenyl)-9-methyl-6H-thieno[3,2-f][1,2,4]triazolo[4,3-a][1,4]diazepin-2-yl]-2-propynyl}phenanthridin-6(5H)-one
   and the LTD$_4$ antagonist is (E)-4-[3-[2-(4-cyclobutyl-2-thiazolyl)ethenyl]phenylamino]-2,2-diethyl-4-oxobutanoic acid and an inert pharmaceutical carrier.

2. A method of treating allergic reactions which comprises administering to a host requiring such treatment a composition comprising an effective amount of a PAF antagonist and an effective amount of a LTD$_4$ antagonist, wherein the PAF antagonist is 5-{3-[4-(2-chlorophenyl)-9-methyl-6H-thieno[3,2-f][1,2,4]triazolo[4,3-a][1,4]diazepin-2-yl]-2-propynyl}phenanthridin-6(5H)-one
   and the LTD$_4$ antagonist is (E)-4-[3-[2-(4-cyclobutyl-2-thiazolyl)ethenyl]phenylamino]-2,2-diethyl-4-oxobutanoic acid.

* * * * *